United States Patent [19]

Slovacek et al.

[11] Patent Number: 5,156,976
[45] Date of Patent: Oct. 20, 1992

[54] EVANESCENT WAVE SENSOR SHELL AND APPARATUS

[75] Inventors: Rudolf E. Slovacek, Norfolk, Mass.; Walter F. Love, Horseheads, N.Y.

[73] Assignee: Ciba Corning Diagnostics Corp., Medfield, Mass.

[21] Appl. No.: 712,003

[22] Filed: Jun. 7, 1991

[51] Int. Cl.$^5$ .................... G01N 21/00; G01N 21/01; G01N 21/76; G01N 33/543

[52] U.S. Cl. ................................. 436/164; 436/172; 436/518; 436/805; 436/807; 422/82.05; 422/82.08; 422/82.11; 435/808; 356/244

[58] Field of Search ............... 422/82.08, 82.05, 82.11; 436/164, 172, 518, 805, 807; 435/808, 968; 385/12

[56] References Cited

U.S. PATENT DOCUMENTS

| | | | |
|---|---|---|---|
| 3,490,847 | 1/1970 | Berz et al. | 356/300 |
| 3,669,545 | 6/1972 | Gilby | 356/246 |
| 3,733,130 | 5/1973 | Young | 356/244 |
| 4,602,869 | 7/1986 | Harrick et al. | 346/244 |
| 4,671,938 | 6/1987 | Cook | 422/57 |
| 4,730,882 | 3/1988 | Messerschmidt | 356/300 |
| 4,810,658 | 3/1989 | Shanks et al. | 436/172 |
| 4,880,752 | 11/1989 | Keck et al. | 435/7 |
| 5,035,504 | 7/1991 | Milosevic et al. | 356/300 |

OTHER PUBLICATIONS

Wendlandt & Hecht; "Reflectance Spectroscopy"; Interscience Publishers, 1966 pp. 169-191.
Harrick, "Multiple Reflection Cells for Internal Reflection Spectrometry", Analytical Chemistry, vol. 36, #1, Jan., 1964.

Primary Examiner—Robert J. Warden
Assistant Examiner—T. A. Trembley
Attorney, Agent, or Firm—Nicholas I. Slepchuk, Jr.; Arthur S. Morgenstern

[57] ABSTRACT

An evanescent wave sensor for use in analyzing a medium, the sensor including a shell having a radiation port at a first end and a base at a second end. The base has a dimension greater than that of the radiation port, and inner and outer wall surfaces of the shell extend between the radiation port and the base. The shell is formed of a material having an index of refraction greater than that of the medium. An apparatus and method for analyzing the medium using the sensor may include a receptacle which defines a chamber about a portion of the shell for contacting the medium to the shell for analysis, optical elements for guiding radiation from a radiation source to the radiation port, and optical elements for guiding fluorescent radiation from the shell to a detector of fluorescent radiation.

50 Claims, 5 Drawing Sheets

EVANESCENT WAVE SENSOR SHELL AND APPARATUS

FIELD OF THE INVENTION

This invention relates to improved evanescent wave sensors for use in spectrophotometric assays of analytes in fluids, and more particularly to such sensors having a shell with inner and outer wall surfaces which propagate radiation between them by total internal reflection.

CROSS-REFERENCES

The following applications, filed concurrently herewith are incorporated herein by reference:

Slovacek et al, U.S. Ser. No. 07/711,783 entitled "Multiple Surface Evanescent Wave Sensor System"; and Slovacek et al, U.S. Ser. No. 07/712,304 entitled "Multiple Output Referencing System for an Evanescent Wave Sensor".

TECHNICAL DISCLOSURE

There are a number of optical devices which propagate radiation by total internal reflection to generate an evanescent wave at the interface of the device and a medium having a lower index of refraction. See Harrick, N.J., Internal Reflection Spectroscopy, Harrick Scientific Corp., Ossining, N.Y. (Third Printing 1987). The evanescent wave is an electromagnetic waveform which typically extends less than a wavelength into the surrounding medium. However, this penetration is sufficient to permit substantial optical interaction between the evanescent wave component and target substance(s) or analytes in the medium. Analyte, as used herein, shall be understood to include any of a variety of chemical and biochemical substances. The analyte sources may include physiological, scientific and industrial (toxic and nontoxic) test media; where the presence, absence or quantity of the analyte in the test medium is sought to be determined; and where, for example, analysis of a physiological analyte is relevant to diagnosis and/or treatment of disease.

One use of optical devices is in the area of fluorescent immunoassays. Presently, such applications include optical waveguides, for example, in the form of fiber optic rods typically coated with either an antibody or an antigen which binds the corresponding antigen or antibody, respectively from a medium or test sample. This coating is applied typically prior to the performance of an immunoassay measurement. In a "sandwich" immunoassay, an antibody is bound to the surface of the fiber optic rod to form a reactant coating, and the device is immersed in a test sample comprising the antigen to be analyzed, if present, and a second antibody, previously labeled by a fluorescent tag. Alternatively, in a "competitive" assay, the fluorescent labeled antigen is first mixed with the antigen in the sample, and the mixture is brought into contact with the rod and the first, bound antibody coating. In either technique, the fluorescently labeled antibody attached to the antigen to form a tagged complex bound to the fiber optic rod by the first antibody or the fluorescently labeled antigen itself combines with the first antibody coated on the fiber optic rod. Light is introduced into the fiber optic rod at a predetermined wavelength band and is propagated along the rod by total internal reflection. The reflection is, of course, not completely total since the fluorescent tag absorbs a small amount of radiation. Alternatively, the attached fluorescent tag, referred to as a fluorophore, is excited by the evanescent wave electromagnetic fields at a first wavelength and fluoresces at a second, longer wavelength. Fluorescence from the excited fluorophore passes into the optical waveguide via a tunneling effect and the portion of the fluorescent radiation which occurs at an angle greater than the critical angle is propagated through the optical waveguide to emerge from an output end.

The use of fiber optic rods in fluorescent immunoassays provides several advantages over the use of glass or plastic microtiter plates into which fluid suspected of containing an analyte is placed. Rather than serving as an optical waveguide, the plate simply contains the fluid and radiation is passed directly through the fluid and the plate to excite a tagged complex. The plate requires separate washing steps to remove unattached analyte and tagged binder, because unbound fluorophores still present in the medium would otherwise be detected. By comparison, the use of the fiber optic rod eliminates the additional washing steps and is therefore faster and easier.

However, fiber optic rods have a number of disadvantages including difficulty in handling the rod during manufacture and its mounting within a test apparatus. Fiber optic rods must be carefully handled because even a tiny nick or scratch in the surface defeats total internal reflection at that region. In defective or damaged rods, radiation escapes from the rod rather than propagating down the entire length of the rod.

Manufacturing fiber optic rods requires a number of processing steps. Typically, fiber optic rods of silica are drawn from a furnace and then cut. These are bundled and potted in wax to enable handling without scratching the surface of the rods. The rods are then recut to length, polished, rewaxed and cleaned. Finally, the rods are coated with a hydrophobic silane to assist attachment of a reactant coating, and the rod is then cured. An antibody or other reactant is then coupled or attached to the rod to form the reactant coating, typically by dipping the rod in an antibody solution.

Another disadvantage of the fiber optic rods is that light must be introduced at an angle into the rod to achieve total internal reflection. The rod must therefore be carefully aligned with an optical system to achieve total internal reflection, resulting in waveguiding of the light. The reflection is, of course, not completely total since the fluorophore absorbs a small amount of radiation. Further, the evanescent wave is generated only at the points where the radiation reflects from the surface of the rod. A 1 mm diameter rod having a length of 50 mm typically achieves only about twenty-two reflections along its length for light near the critical angle, and even fewer reflections for light propagated at lower angles.

Several improved waveguides are described in U.S. Pat. No. 4,880,752; which is incorporated herein by reference. In one construction, the waveguide has an elongated, rod-shaped core having an opening within the core material. A reactant coating is disposed about the opening within the core. The elongated core has the disadvantages mentioned above for solid fiber optic rods, namely difficulty in handling during manufacture, coating and mounting.

SUMMARY OF THE INVENTION

The preferred evanescent wave sensor of the present invention has a shell with a radiation port at one end and a base at the other end. A wall extends between the radiation port and the base to define inner and outer wall surfaces. Radiation introduced through the radiation port bounces (reflects) between the walls as it is internally reflected by those surfaces, when the radiation is introduced at an angle greater than that of the critical angle (relative to a reference line normal to the surface) and a surrounding medium has a lower index of refraction than that of the material forming the shell. The shell has a large surface area for its length, in comparison to fiber optic rods, and therefore is compact.

In one embodiment, the inner wall surface converges to substantially a point centered beneath the radiation port. This arrangement presents an inclined surface to virtually all incoming radiation signals to assist propagation by total internal reflection. The radiation port, which receives incident radiation and passes emission radiation, may be planar, convex, or concave. The shell may have a pyramid shape, such as to form a cone. The interior of the shell is hollow, and the base defines an opening into the interior.

A reactant coating may be disposed on one of the inner and outer wall surfaces when the sensor is for use in an assay of an analyte in a medium, and the reactant coating includes a binder of the analyte such as an immobilized antibody, an immobilized antigen, an enzyme, or other binding molecule. The shell material is transmissive to radiation which can excite fluorescence of a fluorescent tag and is transmissive to fluorescent radiation from the fluorescent tag when fluorescence is monitored. Alternatively, another parameter such as absorption may be monitored.

Preferably, the sensor further includes a handle attached to the base, such as a tab, an annular flange, or other projection which extends away from the base in a direction transverse to that of the inner and outer wall surfaces. The handle enables manipulation of the shell during manufacture, coating with the reagent, and installation in an apparatus for analyzing a medium.

It is also preferable for the shell material to be suitable for manufacture by injection molding. Thus, the shell can be made precisely and cost effectively. Acceptable materials include plastics including polymethylmethacrylate, polystyrene, polycarbonate, or even a moldable glass.

This invention also features apparatus for analyzing a test medium including a shell such as described above and receptacle means for defining a chamber about a portion of the shell to contact the test medium to the shell for analysis. Preferably, the receptacle defines an access port which enables radiation signals to enter into and emerge from the radiation port of the shell. The apparatus may further include means for guiding radiation through the access port from a radiation source, and means for guiding fluorescent radiation from the shell to means for detecting fluorescent radiation. The receptacle may surround the shell and the access port communicates with the chamber. The access port preferably is defined by an inclined surface in the receptacle which converges toward a narrow region disposed below the radiation port of the shell. The inclined surface establishes a well which minimizes the effect of overfilling the chamber. The apparatus may further include means for introducing the test medium to be analyzed into the chamber, and means for establishing a fluid-tight seal between the base of the shell and the receptacle.

OBJECTS OF THE INVENTION

It is among the objects of the invention to provide an improved sensor, apparatus, and method for analyzing test media and, in particular, for conducting fluorescent immunoassays.

Another object of the invention is to provide a sensor having a large surface area for its length.

Yet another object of the invention is to provide a sensor which generates a large number of internal reflections per unit length.

A still further object of the invention is to provide a sensor which is easily alignable with incoming radiation signals so that the radiation enters the sensor at close to the critical angle of the sensor.

A further object of the invention is to provide a sensor which is easier to manipulate and less costly to manufacture.

Yet another object of the invention is to provide such a sensor which may be injection molded.

DESCRIPTION OF THE DRAWINGS

The foregoing and other objects and advantages of the invention will be appreciated more fully from the following further description thereof with reference to the accompanying drawings wherein.

DESCRIPTION OF THE ILLUSTRATIVE EMBODIMENT

A sensor according to this invention and apparatus and method for using the sensor can be accomplished by a shell having a radiation port at a first end and a base at a second end. The base has a dimension greater than that of the radiation port, and inner and outer wall surfaces of the shell extend between the radiation port and the base. Preferably, the wall surfaces are substantially parallel to each other in the direction extending between the radiation port and the base to reflect light between those surfaces by total internal reflection when the radiation signal(s) is/are introduced at an angle greater than that of the critical angle and a surrounding medium has a lower index of refraction than that of the material comprising the shell. The base has a dimension, such as a diameter, greater than that of the radiation port so that the walls of the shell diverge as they approach the base.

Figure 1:
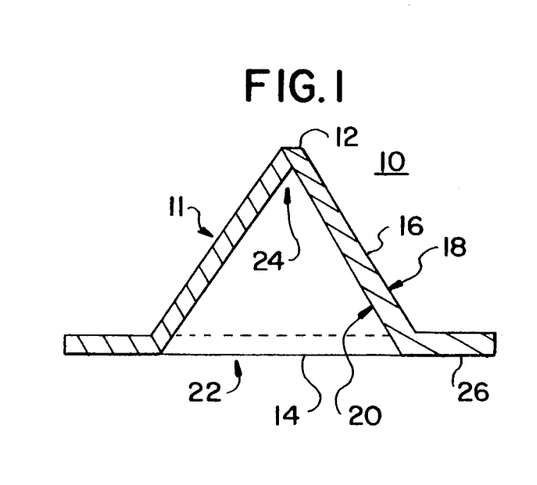
FIG. 1 is a schematic cross-sectional view of a sensor shell according to the invention.

In a preferred construction the sensor shell is frustoconical in shape as shown for sensor 10, FIG. 1, which illustrates a cross-sectional view. The sensor 10 includes a shell or cone 11, having a planar radiation port 12 and base 14. A wall 16 extends between the radiation port 12 and the base 14 and defines outer wall surface 18 and inner wall surface 20. The interior of the shell 11 is hollow and the base 14 defines a circular opening 22 which communicates with the interior. The inner wall 20 converges to a point 24 beneath the radiation port 12 so that virtually all radiation signals entering through radiation port 12 impinges at a desired angle on inner wall surface 20.

In this preferred construction, the sensor 10 further includes handle 26 which is an annular flange connected to the base 14. In other constructions, a tab or other projection may serve as a handle. The handle 26 is a non-active surface, and therefore can be grasped without damaging an optically active surface. In contrast, the radiation port 12 and wall surfaces 18 and 20 are optically active surfaces which are optically polished. Both incoming excitation radiation signals and outgoing fluorescent radiation signals (or other monitored radiation) reflect off the surfaces 18 and 20 without encountering the handle 26. Radiation which exits through the base 14 or the handle 26 will not affect the assay. Although it is preferred that the handle is integral, it need not be integral but can be a separate member attached to the sensor.

Alternatively, the lower portion of the shell 11 can be designated as a handle and not used as an optically active area. One technique for holding a sensor without interfering with the optically active area is disclosed in U.S. Pat. No. 4,671,938; which is incorporated herein by reference.

The dimensions for the sensor 10 in the preferred embodiment are as follows. The radiation port 10 has an outer diameter of 0.92 mm, and the base 14 has an outer diameter of 10.26 mm. The handle 26 has an outer diameter of 16 mm which provides approximately 5 mm of graspable surface along all sides of the shell 11. The sensor 10 is approximately 11.5 mm in length, including a thickness of 0.5 mm for the handle 26. The wall 16 also has a uniform wall thickness of 0.5 mm to provide a large number of internal reflections along its length. The material is polymethylmethacrylate (PMMA) having an index of refraction of 1.4917 at a wavelength of 589.3 nm.

The sensor 10, in comparison to fiber optic rods used in the art, has a large surface area for its length. For the above-described sensor having a length 11.0 mm exclusive of the thickness of the handle 26, the outer wall surface 18 has an area of approximately 170 mm². This area is slightly greater than the 157 mm² of a 50 mm fiber optic rod having a diameter of 1 mm as is presently used in fluorescent immunoassays.

There are several factors to be considered in selecting material for the sensor 10. It is most preferred that the material be injection moldable so that the sensor may by rapidly and inexpensively formed, and easily mass produced. Further, optically polishing the mold will establish optically polished surfaces which do not require further polishing following manufacture. Another factor is that the material must have an index of refraction greater than that of the intended medium to be analyzed, as described below. Additionally, it is desirable for the material to be optically pure and provide low attenuation of the radiation of interest. Silica glass is suitable for ultraviolet or visible radiation, plastics such as polymethyl methacrylate (PMMA), polystyrene, and polycarbonate are suitable for visible radiation, and fluoride glass or chalcogenide are suitable for near infrared radiation. Other organic polymeric materials such as silicones, acrylates, fluoroacrylates, and the like can also be used as the sensor material. It is also desirable for the material to be nonfluorescent to the radiation of interest for assays involving fluorescence.

Additionally, it is desirable for the material to have suitable surface properties or characteristics for binding of a reactant coating to it, or to be amendable to modification to assist bonding. PMMA is preferred not only for its optical purity and its injection molding characteristics, but also because it is hydrophobic which enables antibodies and proteins to be attached to the surface simply by bringing them in contact with the PMMA. For glass, it is desirable to add a silane coating to provide either a hydrophobic surface or one amendable to covalent coupling chemistries.

Figures 2A, 2B, 2C:
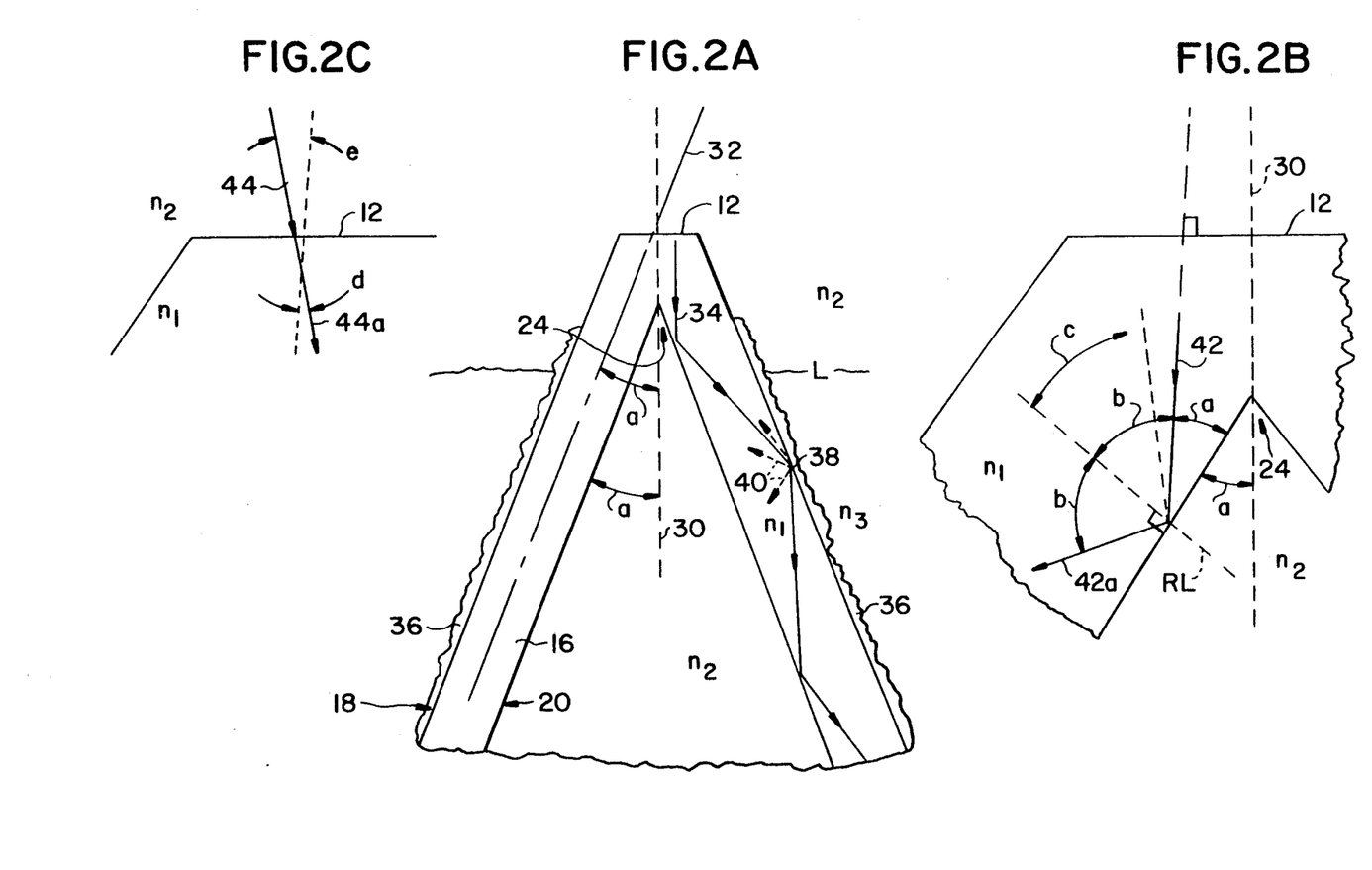
FIG. 2A is a schematic side view of a portion of the sensor of FIG. 1 inserted within a test medium to be analyzed.
FIG. 2B is an enlarged schematic view of total internal reflection of radiation having an angle greater than that of the critical angle, relative to a reference line normal to the surface.
FIG. 2C is a schematic representation of the refraction of radiation entering the sensor.

The shell 10 has an angle a as shown in FIG. 2A. Angle a represents the inclination of the axis of propagation 32 relative to the cone axis 30 which passes through the center of the radiation port 12 and the base 14. The axis of propagation 32 passes through the center of wall 16, halfway between outer wall surface 18 and inner wall surfaces 18, 20 and the cone axis 30 is also angle a.

Light ray 34 is shown propagating through the wall 16 after passing through the port 12, and bouncing between inner wall surface 20 and outer wall surface 18 due to total internal reflection. Total internal reflection occurs when the angle of the ray 34 is greater than the critical angle, which in turn depends upon the index of refraction $n_1$ of the wall 16 relative to the index of refraction $n_2$ of a first medium, typically air, through which radiation passes to enter and exit the radiation port 12, and the index of refraction $n_3$ of a sample medium, typically a fluid L, i.e. a liquid, which surrounds a lower portion of the sensor 10. In the construction shown in FIG. 2A, air surrounds the remainder of the shell 11 including radiation port 12 and all of the inner wall surface 20. The relative indices of refraction, the calculation of the critical angle, and the desired angle of the radiation entering and propagating through the sensor are described in more detail below.

In this construction, the fluid L is contacted to a portion of the outer wall 18, which is coated with a reactant coating 36 which may be an immobilized antibody, an antigen, a receptor, a nucleic acid, an enzyme, or other binding substance as is known in the art. Coating as used herein shall be understood to include specific and nonspecific reactions including noncovalent binding and covalent binding. It is desirable for the reactant coating to bind an analyte in the sample medium or test sample. To prepare a sensor formed of PMMA for use in a sandwich immunoassay, a first antibody is attached to the sensor by dip coating after cleaning the outer wall surface 18 by sonicating the sensor for several seconds while it is immersed in a Freon TF bath. A typical antibody has a height of approximately 100 angstroms (A) and binds and antigen having a typical thickness of 100–200 A in the case of a large molecular weight antigen. A second antibody having an attached fluorophore label is then contacted against the antigen to form a tagged complex having a fluorophore spaced approximately 300-400 A from the surface of the outer wall 18. When a light ray 34 bounces against the surface of the wall 18, as shown for point 38, an evanescent wave excites the fluorophore which induces emission at a longer wavelength. The fluorescent emission is indicated by rays 40, shown in phantom. The portion of the rays 40 which are internally reflected are propagated back through the radiation port 12 in the described embodiment, and detected as described below. This portion depends strongly on the distance of the fluorophore from the PMMA/sample medium interface, and decreases rapidly with increasing distance as expected for a tunneling-like effect.

The parameters of a particular cone construction according to the invention are as follows. The critical angle c relative to reference line RL of FIG. 2B, is calculated according to the formula:

$$c = \sin^{-1}(n_2/n_1)$$

where $n_1$ is the index of refraction of the shell and $n_2$ is the index of refraction of the first medium (air) contacting the interior of the shell. When the index of refraction $n_3$ of the sample medium (the test sample to be analyzed) is greater than $n_2$, then $n_3$ is used as described below.

Radiation having an angle greater than that of angle c, such as angle b of ray 42, will be totally internally reflected as shown by ray 42a. A plastic material such as PMMA has an index of refraction $n_D$ of approximately 1.49 and fused silica has index of refraction of approximately 1.46. For the media surrounding the sensor, air has an index of refraction of approximately 1.00, whereas many biological liquids have an index of refraction of approximately 1.33. For analysis of such liquids, it is therefore desirable for the sensor to have an index of refraction of greater than 1.33. Likewise for the analysis of solid coatings, the sensor material index ($n_1$) must be greater than index $n_3$ or that associated with a solid coating of interest. By way of example, a polystyrene sensor having $n_D = 1.59$ may be utilized in evanescent wave interrogation of methyl cellulose ($n_d = 1.49$) or natural rubber ($n_D = 1.52$) polymeric coatings.

Alternatively, the test sample to be analyzed may be contained in a gas or a liquid phase which is exposed to a solid composite construction. For example, a solid silicone containing a fluorescent material such as a ruthenium-based dye is coated onto the outer surface of a PMMA sensor as a layer having a thickness of 1-10 microns. The sensor is then exposed to another test medium such as blood or gas, and the oxygen contained therein diffusing into the silicone layer quenches (reduces) the fluorescence of the dye. The amount of quenching affects the level of detected fluorescence. Silicone has an index of refraction of approximately 1.43, and therefore the sensor substrate in this application requires an index of refraction greater than 1.43 for waveguiding and evanescent pumping of the silicone layer. In this case the evanescent wave does not propagate into the gas or blood sample, rather the interaction is confined to a fraction of a wavelength depth into the silicone coating layer. In other words, the reactant coating has a low refractive index and a sufficient thickness so as to preclude direct interaction of light between the sensor and the medium to be analyzed. The critical angle c would thus be calculated to be $\sin^{-1}(1.43/1.49) = 73.7°$ for dye-doped silicone and PMMA. It is to be noted that a reactant coating typically is sufficiently thin so that it does not noticeably refract radiation passing through it, especially when the reactant coating is in a fully hydrated state. Otherwise, the effect of the reactant coating must be accounted for.

Because the critical angle is greater at the interface of the sensor and the fluid L than that of the sensor-air interface, in the case of a liquid based sensor, the critical angle defined by the sensor substrate and the measured fluid L is used to establish the minimum acceptable angle of a ray 42. For example, where the fluid to be analyzed is a liquid having an index of refraction $n_D$ of 1.33 and the sensor is formed of PMMA having index of refraction $n_D$ of 1.49 at a wavelength of 589.3 nm, the critical angle is 63.2°. To allow a deviation in angle of up to 3.8°, angle b is selected to be 67°. Subtracting this angle from 90° establishes angle a as 23°.

Next, an acceptable launch angle e is calculated as shown in FIG. 2C. A light ray 44 has an angle of refraction d according to Snell's Law:

$$n_2 \sin e = n_1 \sin d$$

If angle d is allowed to be as large as 3.8°, angle e is 5.6°.

In summary, the cone is constructed by selecting the index of refraction of the cone material and the test medium to be analyzed, and determining the critical angle at the interface of the cone and the test medium for waveguiding of radiation signals at the desired wavelength. The cone angle is calculated with respect to the axis of propagation by subtracting the critical angle from 90°. For a collimated radiation source, this angle may, in principle, be used. However, in practice, the cone apex angle is made somewhat less to account for misalignments and mechanical tolerances. If there is an angle of incidence at the radiation port 12 of greater than 0°, the cone apex angle is reduced to make the walls steeper. The length of the cone is selected to provide the required surface area. It is desirable to form the walls of the shell as thin as possible to increase the number of reflections between the outer and inner wall surfaces, and it is desirable for the radiation signals introduced into the cone to be as close to the critical angle as possible, but still within the waveguiding angle(s), to maximize the evanescent wave component delivered to the interface of the shell and the medium.

Figure 3:
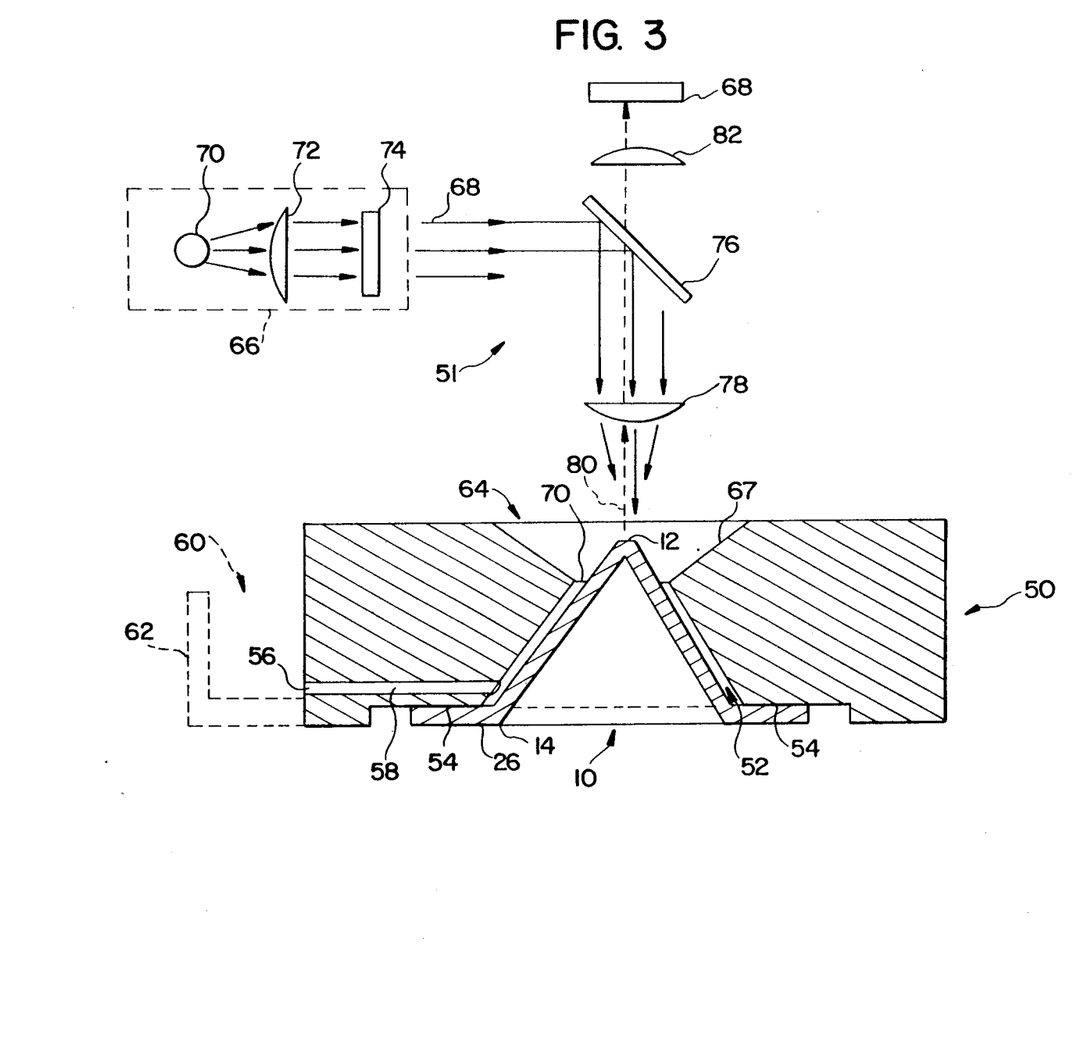
FIG. 3 is a schematic representation of a sensing apparatus according to the invention.

A receptacle 50 for defining a chamber about a sensor 10 and an optical system 51 for delivering radiation signals to and collecting radiation signals from the sensor are shown in FIG. 3. The receptacle 50 defines a chamber 52 into which fluid to be analyzed is delivered. A fluid-tight seal is established between the base 14 and the receptacle 50 by a weld 54 which is formed by sonically welding the handle 26 to the receptacle 50. The receptacle 50 and the sensor 10 in the above construction form a disposable cartridge suitable for one time use. When the sensor is intended for reuse, a removable seal may be established using an o-ring and a clamp, for example. In either case, the attachment 54 is made to a non-active surface which does not affect sensor performance.

Fluid to be analyzed is introduced into the chamber 52 through an introduction port 56 and a passage 58. The test sample may be injected through introduction port 56 using a syringe, or a well 60 may be provided having a wall 62, shown in phantom. In the later construction, liquid to be analyzed is poured into the well 60 and is drawn by capillary action through the passage 58 and upwardly through the chamber 52. The walls of the chamber match the shape of the sensor 10 to minimize the volume of the chamber. In one construction, the gap between the outer wall surface 18 and the receptacle is 0.25 mm with a fluid level height of 10 mm, and the chamber has a working volume of approximately 0.05 ml.

The receptacle 50 further defines an access port 64 which enable the radiation port 12 to communicate with radiation source 66 and detector 68. In this construction, the access port 64 also serves another function. The inclined surface 67 diverges away from narrowed region 70 which serves to limit capillary action beyond the narrowed region 70. Further, the widened area accommodates excess liquid which may be introduced into the chamber 52. Providing an overflow area avoids contaminating the radiation port 12 and minimizes the surface area of the core which is exposed to the excess liquid. Even if overfilling raises the level of the liquid by a millimeter, the surface area of the additionally exposed region of the sensor 10 is far less than the surface area that would be exposed without the widened region of the access port 64, and is also far less than that which would be exposed if a corresponding length of the sensor toward the base of the cone were exposed. These are advantages which result from introducing liquid near the base of the cone and providing an overflow region near the apex of the cone.

The radiation source 66 supplies collimated radiation 68 at a desired wavelength. In one construction, the radiation source 66 is a laser. Alternatively, noncollimated radiation is provided by an element 70 such as a light emitting diode, a halogen lamp, or a flash lamp. Noncollimated radiation is collected by lens 72 and passed through an interference filter 74 to provide collimated radiation at the desired wavelength. The radiation 68 is reflected by beam splitter 76 and passed through launch lens 78 which focuses the radiation upon radiation port 12 of the sensor 10. Fluorescent radiation 80 to be detected emerges through the radiation port 12 and is directed by the lens 78 through the beam splitter 76 and collection lens 82 which in turn impinges the radiation upon the detector 68.

Figure 4:
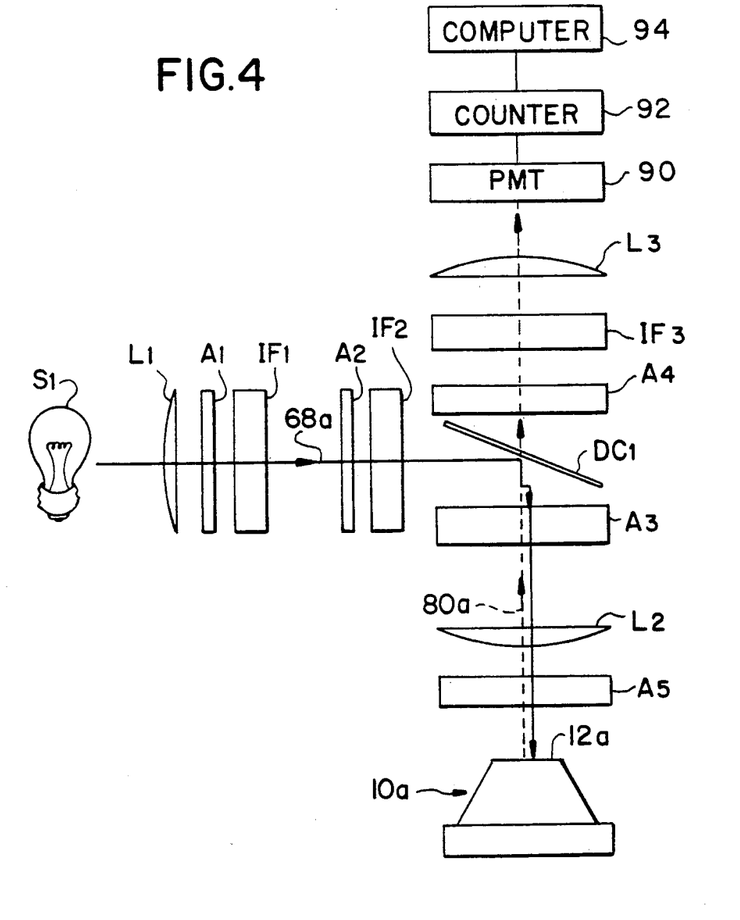
FIG. 4 is a more detailed illustration of the optical components for one embodiment of the apparatus.

A more detailed illustration of an optical system for use with the apparatus according to the invention is shown in FIG. 4. Light from a 3,200° K. tungsten halogen source S1 is collected by a 25 mm focal length plane convex lens L1 which is uncoated. The beam diameter throughout the system (above lens L2) is narrowed to 5 mm by apertures A1, A2, A3, and A4. Omega Optical Inc. 485/22nm interference filters IF1 and IF2 pass blue excitation light at the wavelength of 463 nm to 507 nm. The excitation light 68a is reflected off an Omega 510 dichroic element DCl and which then passes through aperture A3, lens $L_2$ having a focal length of 25 mm, and aperture A5 having an opening of 1 mm. A circular spot 0.8 mm in diameter is projected on the radiation port 12a at an incident angle of less than 5.85°.

When a tagged complex on the surface of the sensor 10a of FIG. 4 includes fluorescein as the fluorophore, then fluorescence radiation is generated in the green spectrum at approximately 520 nm. Note if other fluorophores such as B-phycoerythrin or TEXAS RED$^R$ are used in place of fluorescein, alternative interference filters and dichroic elements would be required to match the dye excitation and emission characteristics.

The fluorescence radiation 80a returns through aperture A5, lens $L_2$, aperture A3, and passes through the dichroic element DCl. The beam is narrowed by aperture A4 and wavelengths other than that of interest are blocked by Omega 530/30 nm interference filter IF3. Radiation 80a is then focused by lens L3 having a focal length of 30 mm onto a photomultiplier tube 90, model no. 1527 available from Hammamatsu. The photomultiplier tube is operated at 800 volts and the output is counted by a counter 92, such as model 1112 photon counter available from the manufacturer EG&G. The analog output of the counter 90 is digitized and either plotted or stored in a computer 94.

Figure 5:
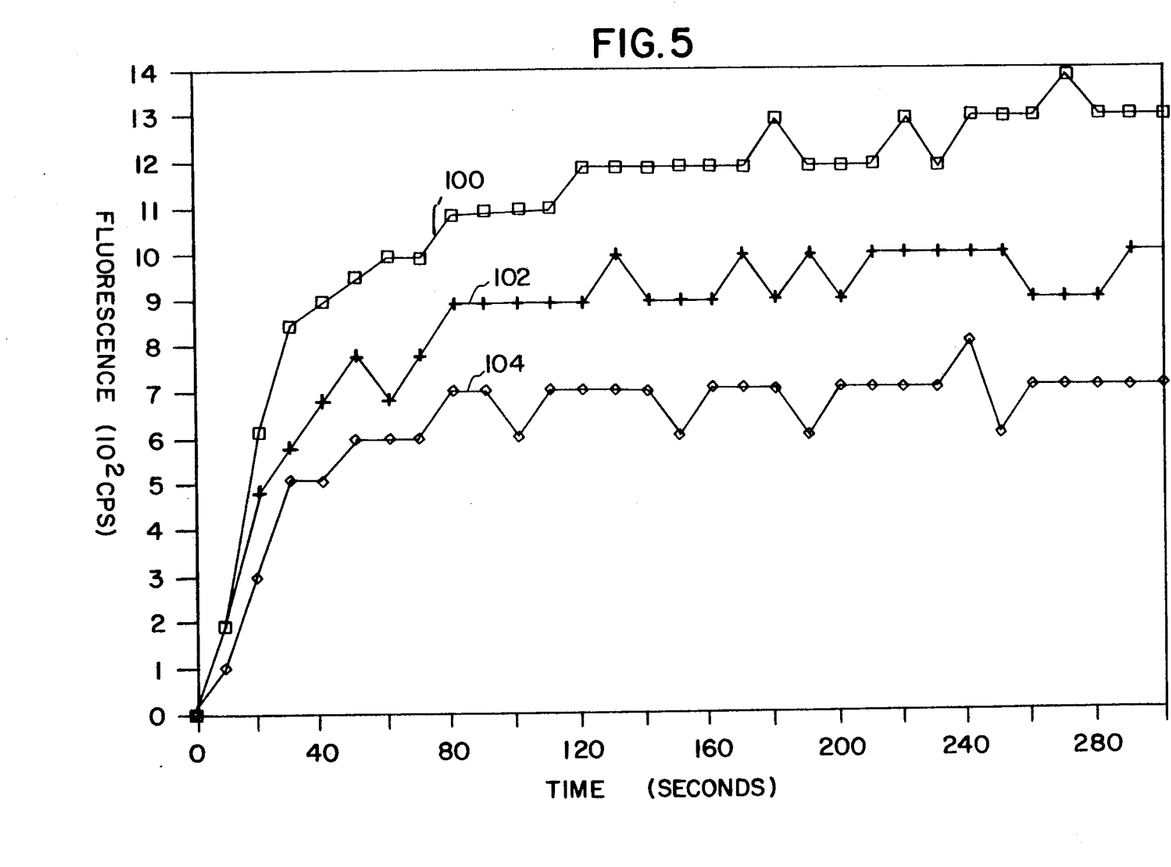
FIG. 5 is a chart of counts (in hundreds) per second (CPS) over time for binding of different concentrations of labelled digoxin using the apparatus of FIG. 4.

An example of three competitive displacement fluorescent immunoassays conducted with the system of FIG. 4 are shown in FIG. 5. The three curves 100, 102 and 104 illustrate kinetic displacement in detected photon counts (in hundreds) per second versus time in seconds. All sensors had approximately $2.88 \times 10^{-16}$ moles/mm$^2$ binding sites. The surface binding site capacity was established by selecting a ratio of nonspecific rabbit IgG to specific anti-digoxin antibody. Antibodies in the selected ratio were attached to the outer wall of the sensor by hydrophobic bonding. All three assays were conducted using 2.93 ng/ml fluoresceinated digoxin conjugate plus a nonlabelled digoxin standard. The curve 100 represents use of a standard of 0 ng/ml digoxin, curve 102 represents use of a digoxin standard of 5.0 ng/ml, and curve 104 represents use of a digoxin standard of 10.0 ng/ml. It can be seen that the greater the concentration of nonlabelled digoxin in the standard, the lower the observed counts, which is the expected result from a competitive immunoassay. The displacement occurs rapidly and can be observed within the first several minutes.

Figure 6A:
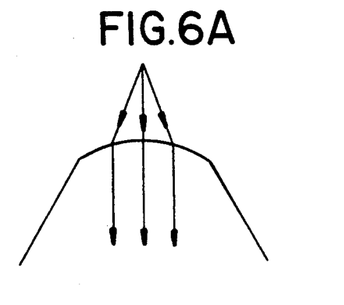
FIGS. 6A and 6B are schematic representations of convex and concave surfaces, respectively, of the radiation port of alternative embodiments of the sensor.
Figure 6B:
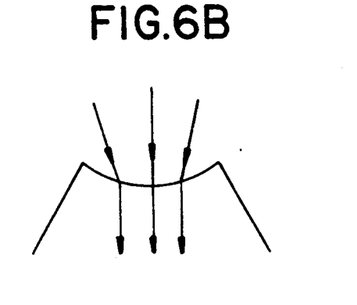

While the sensor is described above as the frustoconical shell having a planar radiation port, these are not limitations of the invention. The radiation port may have a convex surface as shown in FIG. 6A, or a concave surface as shown in FIG. 6B to assist aligning incoming radiation at the desired angle. The base portion of the cone may not be used as a support for the cone; the cone could be mounted in any position. Further, non-conical sensor shapes are acceptable, such as a pyramid shape having a base with a greater width than that of the radiation port. For example, the pyramid can have a base in the form of a regular or nonregular polygon such as a triangle, quadrangle, or any number of sides from two (if the sides are curved) to twenty, or more. Preferably, the walls extend up to converge at a radiation port which distributes the radiation waves evenly about the entire device, that is, over a 360° path. The conical shape is preferred, however, because it contains fewer corners and edges at which radiation may escape rather than be totally internally reflected. Two or more materials may be used to form the shell, and one or more of the materials may not be transparent to radiation. Moreover, a reactant coating may be disposed on the inner surface instead of, or in addition to, being disposed on the outer surface of the sensor.

Figure 7A:
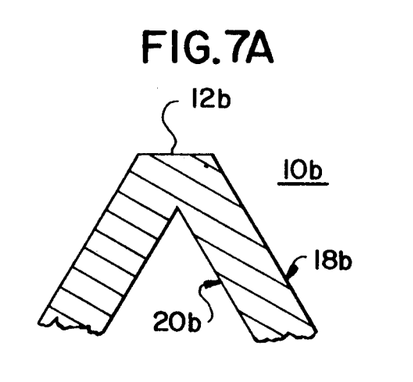
FIGS. 7A and 7B are schematic partial cross-sectional views of sensor shells having converging and diverging wall surfaces, respectively.
Figure 7B:
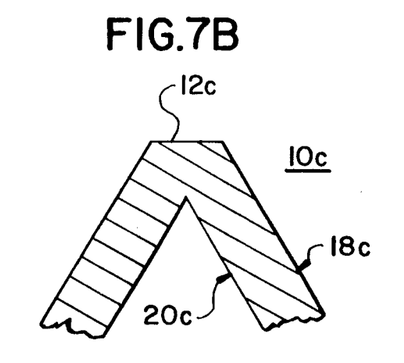

Although the inner and outer wall surfaces are described above as being substantially parallel, the invention is not so limited. Sensor 10b, FIG. 7A, has outer wall surface 18b and inner wall surface 20b which converge toward each other as they extend away from radiation port 12b. The angle of light propagating between converging surfaces 18b, 20b becomes increasingly smaller relative to the critical angle, that is, the angle approaches the critical angle. Eventually, the light signal will exit the sensor 10b when its angle becomes less than the critical angle. The converging wall surfaces can be formed along part or all of the length of the sensor 10b to focus the radiation and to increase the mechanical integrity of the shell near the radiation port 12b. Conversely, a sensor 10c, FIG. 7B, is provided with diverging surfaces 18c, 20c which diverge as they extend away from radiation port 12c. In this configuration, the angle of the propagating radiation signal becomes increasingly large relative to the critical angle, which would serve to defocus the propagated radiation. The sensor 10c has increased wall thickness at the lower portion of the sensor, and therefore increased mechanical integrity in that region.

Although specific features of the invention are shown in some drawings and not in others, it is for convenience only as each feature may be combined with any or all of the other features in accordance with the invention.

It should be understood that the foregoing description of the invention is intended merely to be illustrative thereof and that other modification, embodiments, and equivalents may be apparent to those skilled in the art without departing from its spirit.

We claim:

1. An evanescent wave sensor for analyzing a test medium, comprising:
   a shell having a radiation port at a first end and a base at a second end, the base having a dimension greater than that of the radiation port;
   inner and outer wall surfaces of the shell extending between the radiation port and the base; and
   the shell being formed of a material having a predetermined index of refraction greater than that of the test medium in which the shell is to be used.

2. The sensor of claim 1 in which the inner wall surface converges substantially to a point and is positioned beneath a center of the radiation port.

3. The sensor of claim 1 in which the radiation port is a planar surface.

4. The sensor of claim 1 in which the radiation port is convex.

5. The sensor of claim 1 in which the radiation port is concave.

6. The sensor of claim 1 in which the inner and outer wall surfaces propagate radiation signals between them by total internal reflection along an axis of propagation and the inner and outer wall surfaces are substantially parallel to each other along the axis of propagation.

7. The sensor of claim 6 in which the shell has an axis extending through the center of the radiation port and the base, and the inner and outer wall surfaces are curved along a direction transverse to the shell axis.

8. The sensor of claim 1 in which the shell is frustoconical in shape.

9. The sensor of claim 1 in which the base defines an opening into the interior of the shell.

10. The sensor of claim 1 further including a reactant coating disposed on at least one of the inner and outer wall surfaces.

11. The sensor of claim 10 in which the sensor is for use in an assay of at least one analyte in the test medium and the reactant coating includes a binding partner of one or more analyte(s).

12. The sensor of claim 11 is which the reactant coating is an immobilized antibody.

13. The sensor of claim 11 in which the reactant coating is an immobilized antigen.

14. The sensor of claim 11 in which the reactant coating is an enzyme.

15. The sensor of claim 11 in which the reactant coating is a nucleic acid.

16. The sensor of claim 11 in which the reactant coating is a receptor.

17. The sensor of claim 11 in which the reactant coating is a binding molecule.

18. The sensor of claim 11 in which the shell material is transmissive to radiation signals which can excite fluorescence of a fluorescent tag and is transmissive to fluorescent radiation from the fluorescent tag.

19. The sensor of claim 18 wherein a fluorescent tag is bound to the binding partner for the analyte.

20. The sensor of claim 1 further including handle means, attached to the base, for enabling manipulation of the shell.

21. The sensor of claim 20 in which the handle means includes a projection extending away from the base transversely to the inner and outer wall surfaces.

22. The sensor of claim 20 in which the handle means includes a flange disposed about the periphery of the base.

23. The sensor of claim 22 in which the flange is annular.

24. The sensor of claim 1 in which the shell material is injection molded.

25. The sensor of claim 1 in which the material of the shell is polymethyl methacrylate.

26. The sensor of claim 1 in which the shell is disposable after each analysis.

27. A conical evanescent wave sensor for use in a fluorescence assay of at least one analyte suspected of being present in a test sample, comprising:
    a conical shell having a radiation port at a first end and a base at the second end, the base having a diameter greater than that of the radiation port; and
    curved inner and outer wall surfaces of the shell for propagating radiation signals by total internal reflection between them along an axis of propagation, the surfaces extending between the radiation port and the base.

28. The sensor of claim 27 wherein said sensor further comprises handle means attached to the base, for enabling manipulation of the shell.

29. The sensor of claim 28 in which the handle means includes an annular flange disposed about the periphery of the base.

30. The sensor of claim 27 in which the inner and outer wall surfaces are substantially parallel to each other along the axis of propagation.

31. The sensor of claim 27 in which the inner and outer wall surfaces are nonparallel to each other along the axis of propagation.

32. The sensor of claim 27 in which the shell is formed of a material having a greater index of refraction than that of the test sample.

33. The sensor of claim 32 in which the test sample to be analyzed is a liquid and the material has an index of refraction greater than 1.33.

34. The sensor of claim 27 further including at least one reactant coating disposed on one of the inner and outer wall surfaces for interacting with at least one analyte.

35. The sensor of claim 34 in which the shell material is transmissive to radiation which can excite fluorescence of a fluorescent tag and transmissive to fluorescent radiation from the fluorescent tag.

36. The sensor of claim 27 further including at least one reactant coating disposed on one of the inner and outer wall surfaces for interacting with at least one analyte, each reactant coating having a low refractive index and a sufficient thickness so as to preclude direct interaction of light signals between the sensor and the test sample.

37. The sensor of claim 27 in which the inner wall surface converges to substantially a point beneath the radiation port.

38. An apparatus for analyzing a medium, comprising:
a shell having a radiation port at a first end and a base at a second end, the base having a dimension greater than that of the radiation port;
inner and outer wall surfaces of the shell extending between the radiation port and the base;
the shell being formed of a material having a greater index of refraction than that of the medium; and
receptacle means for defining a chamber about a portion of the shell for contacting th medium with the shell for analysis.

39. The apparatus of claim 38 in which the receptacle means defines a access port for enabling passage of radiation signals to and from the radiation port of the shell.

40. The apparatus of claim 39 in which the receptacle means surrounds the shell and the access port communicates with the chamber.

41. The apparatus of claim 40 in which the access port is defined by an inclined surface which converges toward a narrow region disposed below the radiation port of the shell.

42. The apparatus of claim 38 in which the inner and outer wall surfaces propagate radiation signals between them by total internal reflection along an axis of propagation, and the surfaces are substantially parallel to each other along the axis of propagation.

43. The apparatus of claim 38 in which the receptacle means includes means for introducing the medium into the chamber.

44. The apparatus of claim 38 further including means for establishing a fluid-tight seal between the base of the shell and the receptacle means.

45. The apparatus of claim 38 further including:
means for guiding radiation through the access port from a radiation source to the radiation port such that the radiation is propagated between the inner and outer wall surfaces of the shell; and
means for guiding fluorescent radiation from the shell to means for detecting fluorescent radiation.

46. An apparatus for spectrophotometrically assaying at least one analyte in a fluid, the apparatus comprising:
a shell having a radiation port at a first end and a base at a second end, the base having a dimension greater than that of the radiation port;
inner and outer wall surfaces of the shell for propagating radiation by total internal reflection along an axis of propagation, the surfaces extending between the radiation port and the base;
the shell being formed of a material having a greater index of refraction than that of the fluid;
means for guiding radiation from a radiation source to the radiation port such that the radiation is propagated along the axis of propagation; and
means for guiding fluorescent radiation from the shell to means for detecting fluorescent radiation.

47. A method of assaying at least one analyte in a medium, comprising:
providing a sensor having a shell with a radiation port at a first end and a base at a second end, the base having a dimension greater than that of the radiation port, the shell further including inner and outer wall surfaces for propagating radiation by total internal reflection between them along an axis of propagation, and the shell being formed of a material having a greater index of refraction than that of the medium to be analyzed;
contacting the sensor with the medium;
propagating radiation down the shell between the inner and outer wall surfaces to irradiate the medium; and
detecting radiation reentering the shell and emitted from the radiation port.

48. A method of spectrophotometrically assaying at least one analyte in a medium, comprising:
providing a sensor having a shell with a radiation port at a first end and a base at a second end, the base having a dimension greater than that of the radiation port, the shell further including inner and outer wall surfaces for propagating one or more radiation signals by total internal reflection between them along an axis of propagation, at least one reactant coating disposed on at least one of the inner and outer wall surfaces for interacting with at least one analyte suspected of being present in the medium and the shell being formed of a material having a greater index of refraction than that of the medium to be analyzed;
contacting the sensor with the medium;
propagating one or more radiation signals down the shell to irradiate the interacting analyte and reactant coating; and
detecting one or more radiation signals resulting from the irradiation of the analyte interaction by monitoring one or more radiation signals emitted from the radiation port.

49. The method of claim 48 wherein the sensor is further contacted by a fluorescently tagged binding partner of said analyte.

50. The method of claim 48 in which the radiation propagated down the shell induces fluorescence upon irradiation the interacting analyte and reactant coating, and detecting includes monitoring fluorescent radiation emitted from the radiation port.

* * * * *